United States Patent [19]

Kodama et al.

[11] Patent Number: 5,171,738

[45] Date of Patent: Dec. 15, 1992

[54] METHOD OF TREATING MALIGNANT TUMORS

[75] Inventors: Masashi Kodama, Shiga; Yutaka Katayama, deceased, late of Kyoto, by Takako Katayama, heir; by Shigemasa Katayama, heir; by Nobuko Katayama, heir, both of Tokyo; by Yoshimasa Katayama, heir, Kyoto; Toru Tani, Shiga; Kazuo Teramoto, Shiga; Mutsuo Murakami, Shiga, all of Japan

[73] Assignee: Toray Industries, Inc., Tokyo, Japan

[21] Appl. No.: 401,502

[22] Filed: Aug. 30, 1989

Related U.S. Application Data

[63] Continuation-in-part of Ser. No. 315,259, Feb. 23, 1989, abandoned, which is a continuation of Ser. No. 54,049, May 26, 1987, abandoned, which is a continuation of Ser. No. 804,319, Dec. 3, 1985, abandoned, which is a continuation of Ser. No. 536,973, Sep. 29, 1983, abandoned.

[30] Foreign Application Priority Data

Oct. 4, 1982 [JP] Japan ................................ 57-173321
May 16, 1983 [JP] Japan ................................ 58-84197

[51] Int. Cl.⁵ .................. A61K 31/715; A61K 31/74; A61K 31/79; A61K 31/78
[52] U.S. Cl. .................... 424/78.17; 514/57; 514/54; 424/78.18
[58] Field of Search ......................... 514/53, 54, 57; 536/55.1, 55.3; 424/78, 80, 81, 83

[56] References Cited

U.S. PATENT DOCUMENTS

| | | | |
|---|---|---|---|
| 2,294,925 | 9/1942 | Miller | 536/55.3 |
| 2,374,236 | 4/1945 | Salzberg et al. | 536/53 |
| 2,809,190 | 10/1957 | Kelly et al. | 536/53 |
| 4,003,792 | 1/1977 | Mill et al. | 530/303 |
| 4,057,685 | 11/1977 | McIntire | 536/55.1 |
| 4,090,919 | 5/1978 | Chibata et al. | 536/55.1 |
| 4,411,832 | 10/1983 | Cuatrecasas et al. | 536/55.1 |

OTHER PUBLICATIONS

Tani et al., "Efficacy and Biocompatibility of a Novel Anti-Cancer Fiber in Hemoperfusion on Cancer-Bearing Rabbits", Trans. Am. Soc. Artif. Intern. Organs, vol. XXX, 1984, pp. 308–314.

Weinbaum et al., (Eds): *Microbial Toxins*, Chapter 3, "The Physical Structure of Bacterial Lipopolysaccharides" by Shands Jr., vol. IV, Bacterial Endotoxins, Academic Press, N.Y., 1971, pp. 126–129.

Jawetz et al., Chapter 2, "Cell Structure", *Review of Medical Microbiology*, 13th Ed., Maruzen Asion Edition, pp. 16–19.

Abstract of "The Clinical Use of Bacterial Polysaccharides in Malignant Disease", Proc. of the Am. Assoc. Can. Res., 2, 240–241 (1957), p. 240.

Creech et al., "Preparation and Chemical Properties of Polysaccharide–Lipid Complexes Obtained from *Serratia marcescens* and *Escherichia coli*," Cancer Res., 14, 817–823 (1954).

Wetting Agents for Automatic Analyzer, Price List No. 20, Reagents, Nakarai Chemicals, Ltd., 1983.

Tanamoto et al.: "Essential Regions of the Lipopolysaccharide of *Pseudomonas aeruginosa* . . .", J. Biochem. 91, 741–746 (1982).

(List continued on next page.)

*Primary Examiner*—John W. Rollins
*Attorney, Agent, or Firm*—Nixon & Vanderhye

[57] ABSTRACT

Lipopolysaccharides derived from the cell walls of Gram-negative bacteria, also known as endotoxins or pyrogens, are immobilized on a solid, insoluble carrier. The blood, blood plasma or blood serum of a tumor-bearing patient is passed over the immobilized lipopolysaccharide-containing blood treating material to treat the patient's tumor.

3 Claims, 1 Drawing Sheet

OTHER PUBLICATIONS

Raziuddin, "Biological Activities of Chemically Modified Endotoxins from *Vibrio cholerae*," Biochimica et Biophysica Acta, 620 (1980), pp. 193–204.

*Chemical Abstracts*, vol. 94, 1981, p. 135, No. 203551r, by Maitra et al. "Properties of Binding of *Escherichia coli* Endotoxin to Various Matrices" and *J. Clin Microbiol.*, 1981, 13(1), 49–53 Abstract.

*Chemical Abstracts*, vol. 94, 1981, p. 590, No. 137656d, by Raziuddin et al., "Binding of Bacterial Endotoxin (LPS) to Encephalitogenic Myelin Basic Protein and Modulation of Characteristic Biologic Activities of LPS" and *J. Clin. Microbiol.*, 1981, 125(3), 1030–5.

"Immobilized Enzymes", by O. Zaborsky, CRC Press, 1974, pp. 5, 9, 24–26.

*Chemical Abstracts*, vol. 99, No. 3, Jul. 18, 1983, p. 483, No. 20829z, S. Lubinsky-Mink et al., "Interaction of Latex-insolubilized Endotoxins With Murine Macrophages: Phagocytic Responses of Endotoxin-Responsive (C3HeB/FeJ) and Unresponsive (C3H/HeJ) Macrophages in Vitro" and *J. Reticuloendothel. Soc.*, 1983, 33(5), 353–67.

European Search Report.

METHOD OF TREATING MALIGNANT TUMORS

CROSS-REFERENCE TO RELATED APPLICATIONS

This application is a continuation-in-part of earlier application Ser. No. 07/315,259 filed Feb. 23, 1989, now abandoned which, in turn, is a continuation of Ser. No. 07/054,049 filed May 26, 1987, now abandoned, which, in turn, is a continuation of Ser. No. 06/804,319 filed Dec. 3, 1985, now abandoned which, in turn, is a continuation of Ser. No. 06/536,973 filed Sep. 29, 1983 also now abandoned.

FIELD OF THE INVENTION

This invention relates to a blood-treating material having antitumor effect.

DESCRIPTION OF THE PRIOR ART

The most frequent cause of death in developed countries is cancer. However, powerful carcinostatic agents have yet to be found, as contrasted, for example with fully effective antibiotics which are widely used to successfully combat infectious diseases.

Lipopolysaccharides derived from cell walls of Gram-negative bacteria are known substances called "endotoxins" or "pyrogens". It is known that the lipopolysaccharides have harmful effects such as pyrogenic effects, Schwartzman activity and lethal toxicity. It has also been known that they have antitumor effects against malignant tumors.

Substances having anti-tumor effects are in great demand, since specific remedies for malignant tumors have not been developed. However, the lipopolysaccharides cannot be used safely, since their fatal doses are very close to the minimum effective doses in the treatment of malignant tumors.

SUMMARY OF THE INVENTION

Figure 1:
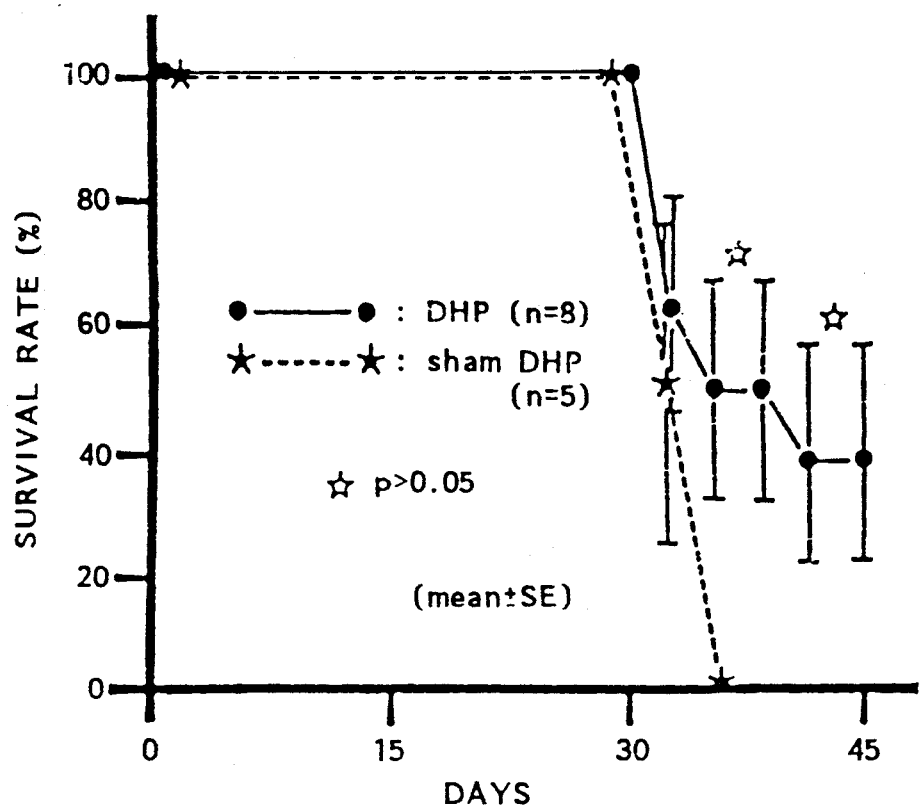
FIG. 1 is a graph showing the survival rate of V×2 tumor-bearing rabbits.

The present invention provides (1) a blood-treating material composed of a lipopoly-saccharide derived from cell walls of Gram-negative bacteria and immobilized by an insoluble carrier containing an amino group or a carboxyl group, and (2) a process for producing the blood-treating material in which a condensing agent is reacted with a mixture of the lipopolysaccharide and the insoluble carrier.

The present invention makes is possible to reduce the lethal toxicity of the above-mentioned lipoplsaccharides and provide new blood-treating materials that can be used safely and effectively for the treatment of cancer, because this blood-treating material has antitumor effects similar to those of the lipopolyaccarides derived from cell walls of Gram-negative bacteria but without the fatal effects.

DETAILED DESCRIPTION OF THE INVENTION

The lipopolysaccharides derived from cell walls of Gram-negative bacteria as described herein are lipid-polysaccaride complexes or lipidpolysaccaride-protein complexes localized in the outer layers of cell walls of Gram-negative bacteria. Typical gram-negative bacterial include Gram-negative cocci, such as Neisseria gonorrhoeae; Gram-negative aerobic bacilli, such as Pseudomonas aeruginosa, Brucella abortus and Bordetella pertussis; and Gram-negative facultative anaerobic bacilli, such as Escherichia coli, Salmonella typhi, Shigella dysenteriae, Klebsiella pneumoniae, Serratia marcescens, Proteus vulgaris, Yersinia enterocolitica and Vibrio cholerae. These lipopolysaccharides can be extracted from the Gram-negative bacteria by known processes. As typical processes, there may be mentioned those of phenol-water extraction (Van Otto Westphal et al., Z. Naturforsch., 7B: 148–155 (1952)), trichloroacetic acid extraction (A. Boivin and L. Meserobeanu., Comp. Rend. Soc. Biol., 128, 5 (1938)), butanol extraction (D. C. Morrison and L. Leive., J. Biol. Chem. 250, (3) 2911 (1975)) and ethylenediaminetetraacetic acid-water extraction (L. Leive et al., J. Biol. Chem., 243, 6384 (1968)). From the viewpoint of providing a material that is convenient to immobilize, it is preferred that the lipopoly-saccharides have a protein content of from about 0.1 to about 50%, particularly about 1 to about 20%. The molecular weights of the lipopoly-saccharides, which vary depending on the measuring method and conditions, generally are in the range of several thousands to several millions, since their molecules are liable to associate with each other.

The insoluble carriers as disclosed herein include substantially insoluble carriers having a primary, secondary, or tertiary amino group, a quaternary ammonium group or a carboxyl group which yield no eluate under conditions of practical use. The insoluble carriers used in the present invention include, for example, (1) polystyrene or styrene/divinybenzene copolymer in which a substituent having a primary, secondary, or tertiary amino group, a quaternary ammonium group or carboxyl group has been introduced into the aromatic nucleus; (2) the same carrier as in the above item (1) but containing methylene-crosslinked or sulfone-crosslinked polystyrene used in place of the polystrene; (3) acrylic acid/acrylonitrile copolymer; (4) acrylic acid/styrene copolymer; (5) nylon 6; (6) nylon 6.6; (7) polyethylene terephthalate; (8) a carboxyl group containing insolubilized cellulose; and (9) aminoethylated cellulose. Among the above-listed classes of carriers those containing a vinyl polymer as the trunk polymer, and particularly those containing a styrene polymer as the trunk polymer, are preferred since they have both high acid and alkali resistance.

The physical form that the insoluble carriers take is not particularly limited provided that they have an adequate surface area and sufficient mechanical strength to withstand an external force during use. Generally, the carriers are used in the form of granules, fibers, hollow filaments, films and membranes.

According to the present invention, the lipopolysaccharide may be immobilized by the insoluble carrier by any suitable process in which the condensation reactivity of the amino or carboxyl group of the insoluble carrier is utilized. The process is not particularly limited. In a typical embodiment of the process (1) a condensing agent for peptide synthesis is added to a mixture of the insoluble carrier and an aqueous solution of the lipopolysaccharide, or (2) a carboxyl group-containing insoluble carrier is treated with an activator such as N-hydroxysuccinimide or 1-hydroxy benzotriazole. Then the condensing agent for peptide synthesis is added and finally the carrier is mixed with the lipopolysaccharide solution. As the condensing agent for the peptide synthesis there may be mentioned 1-ethyl-3-(3-dimentylaminopropyl)-carbodiimide, 1-cyclohexyl-3-(2-morpholinoethyl)-carbodiimide metho-p-toluenesulfonate, N,N'-dicyclo-hexylcarbodiimide and Woodward reagent K.

As for the density of the lipopolysaccharide immobilized by the insoluble carrier according to the present invention, it is desirable to immobilize at least about 10 μg, more preferably about 1 mg of the lipopolysaccharide per square meter of the surface area of the carrier, since if the immobilization density is too low, a large amount of carrier is required. Accordingly, when the insoluble carrier has a surface area of about 0.01 to about 100 m$^2$/g, it is preferred that at least about 0.001, particularly about 0.01, more preferably about 0.1 milliequivalent/g (meq/g) of the primary or secondary amino group or carboxyl group is contained therein.

The blood-treating material of the present invention may be used in such a way that it is charged in an extracorporeal circulation column and contacted with the whole blood or blood plasma of the person receiving antitumor therapy, the contact being continuously or intermittently. Alternatively, the blood-treating material may be charged in an injector or syringe, then the whole blood or plasma is withdrawn from the person's body, contacted with the blood-treating material and the resulting liquid is returned into the body.

The following examples further illustrate the present invention.

EXAMPLE 1

Preparation of The Insoluble Carrier 50 g of an islands-in-sea type composite fiber (having 16 islands, single fiber fineness of 2,6 d, tensile strength of 2.9 g/d, elongation of 50%) comprising 50 parts of a polypropylene (Mitsui Nobrene J3HG) as an island component and a mixture of 46 parts of a polystyrene ("Styron" 666) and 4 parts of a polypropylene (Sumitomo "Noprene WF-727-F) as an island component was immersed in a mixed solution of 50 g of N-methylol-α-chloroacetamide, 400 g of nitrobenzene, 400 g of 98% sulfuric acid and 0.85 g of paraformaldehyde. The mixture was heated at 20° C. for 1 hr. The fiber was taken out from the reaction liquid and plunged into 5 liters of ice water at 0° C. to terminate the reaction. The fiber was washed with water and then nitrobenzene was removed from the fiber by extraction with methanol. The fiber was dried at 50° C. in vacuum to obtain 71 g of chloroacetamidomethylated fiber. Then, 40 g of the fiber was immersed in ethylenediamine at 15° C. and a reaction was carried out at 15° to 20° C. for 24 hr. to obtain ethylenediaminoacetamido-methylated fiber. The fiber contained 1.8 mmol/g of an ethylenediamino group had primary and secondary amino groups but did not have tertiary or quaternary amino groups. The fiber had a water content of 1.0 g per gram (1.0 g) of the dry fiber at pH 7.4. Under these conditions, the single yarn diameter was 40 to 44 μm.

Preparation of the Blood Treating Material 32 g of the above-mentined amino group-containing polystyrene fiber was swollen by immersing the same in 300 ml of water for an entire day and night. The fiber was then mixed with 500 ml of a 0.4 mg/l aqueous solution of a lipopolysaccharide obtained from Escherichia coli 055:B5 (a product of Difco Laboratories Co. obtained by extraction with trichloroacetic acid, the protein content was 10%). Then, 5.0 g of 1-ethyl-3-(3-dimethylaminopropyl) carbodiimide was added thereto in divided portions while the pH of the mixture was maintained at 4.5 to 6.0 with 1N-hydrochloric acid and 1N-sodium hydroxide. A solution thus obtained was shaken at room temperature for 2 days. The fiber was taken out and washed with 1 liter of water three times. The fiber was then immersed in 1 liter of boiling water for 30 min. This immersion was repeated three times. The fiber was washed with a 0.07M phosphate buffer solution (pH 7.4) until the pH of the wash solution became 7.4 to obtain the fiber onto which the lipopolysaccharide was immobilized.

The concentrations of the lipopoly-saccharide in the immobilization mother liquor and the wash solution were determined by the phenol/sulfuric acid method in which 5 ml of concentrated sulfuric acid was added to a mixture of 1 ml of the sample and 1 ml of a 5% aqueous phenol solution and an absorbance of the mixture at 485 mμ was measured. The amount of immobilized lipopolysaccharide was estimated from that of lipopolysaccharide remaining in the mother solution.

The amount of the immobilized lipopoly-saccharide was 5.0 mg/g.

0.6 g of the above-mentioned lipopoly-saccharide-immobilized fiber was washed with 200 ml of isotonic sodium chloride solution according to the Japanese Pharmaceopoeia and then immersed in 50 ml of the same solution. The resulting solution was heated to 38° C. for 3 hr. Thereafter, the amount of the lipopolysaccharide in the isotonic sodium chloride solution was determined by the Limulus-Pregel method. The amount was below 1 ng/ml.

Biological Testing of The Blood Treating Material

Fibrosarcoma MC-BL was induced in BALB/C mice by innoculation with methylcholanthrene. Five hundred thousand tumor cells were taken and subcutaneously injected into the backs of BALB/C mice to obtain tumor-bearing mice. The tumor grew into a size of 2.1 mm diameter 5 days after the inoculation, 6.3 mm 10 days thereafter and 81.9 mm 12 days thereafter.

0.6 g of the above-mentioned lipopoly-saccharide-immobilized fiber (containing 1.0 mg of the lipopolysaccharide prepared in Example 1 was immersed in 20 ml of human plasma at 37° C. for 180 min. The plasma was given to the tumor-bearing mice by intravenous injection 11 days after the innoculation (tumor diameter: 7 mm), 13 days and 15 days after the inoculation in an amount of 0.5 ml each time. In one mouse in the total of 10 mice, the tumor was completely necrotized and disappeared. In the balance (9 mice), a remarkable softening of the tumor was recognized. Experiments similar to the above were carried out using 10 ml of human plasma treated at 56° C. for 30 min. as a control. In the latter case, the necrosis, softening or bleeding of the tumor was not observed at all.

EXAMPLE 2

0.4 g of the lipopolysaccharide-immobilized fiber (2.0 mg of lipopolysaccharide) prepared in Example 1 was immersed in 40 ml of plasma obtained from 100 BALB/C mice at 37° C. for 180 min. The plasma was given to the tumor-bearing mice obtained in the same way as in Example 1 by intravenous injection 11, 13 and 15 days after the inoculation in an amount of 1.0 ml each time. In one mouse in the total of 10 mice, the tumor disappeared completely. In the rest (9 mice), a remarkable softening of the tumor was recognized.

EXAMPLE 3

0.2 g of the lipopolysaccharide-immobilized fiber prepared in Example 1 was immersed in 20 ml of human plasma at 37° C. for 180 min. Nought point five ml portions of the plasma were mixed with 2.5 ml portions of human plasma. The mixture was given to the tumor-bearing mice obtained in the same way as in Example 1 by intraperitoneal injection 11, 13, 15, 17 and 19 days after the inoculation. The tumor disappeared completely in 2 mice in the total of 7 mice.

EXAMPLE 4

Tumor-bearing rabbits were obtained by intradermal injection of $5 \times 10^5$ VX2 tumor cells (suspended in 0.3 ml of phosphate buffered saline containing 10% fetal calf serum) into the backs of New Zealand White rabbits (male).

Blood-treating columns were prepared by filling 0.8 g of bundled blood-treating material or carrier obtained in the same way as in Example 1.

Tumor-bearing rabbits (anesthetized with sodium pentobarbital, intraperitoneal injection) underwent extracorporeal perfusion through the above-mentioned blood-trating columns at a flow rate of 15 ml/min. for 90 minutes by canulation of the carotid and the jugular vein 5 days after inoculation. Heparin (500 U/kg-body-weight of rabbit) was added into the circuit at the beginning of the perfusion. After the suture, the weight of the rabbits and the size of the tumor were observed. Nine tumor-bearing rabbits (group 1) were used for the blood-treating material and five (group 2) were used for the carrier. Six tumor-bearing rabbits (group 3) were observed without extracorporeal perfusion.

The size of the tumor was calculated by the equation: the diameter of the tumor = a×b where a and b are the longest diameter of the tumor and the diameter taken rectangular to the longest diameter, to it respectively.

Changes of tumor-size and weight of rabbits were shown in Table I and II respectively.

These results indicate that the blood-treating material of the present invention is effective for the increase of the weight of the tumor-bearing rabbit as well as a decrease in the tumor size.

TABLE I

| group of rabbits | average diameter of the tumors (mm) time after innoculation (day) | | | | | | |
|---|---|---|---|---|---|---|---|
| | 5 | 10 | 15 | 20 | 25 | 30 | 35 |
| 1* | 9.3 | 10.5 | 11.0 | 12.5 | 9.2 | 7.5 | 7.6 |
| 2 | 9.2 | 11.0 | 14.8 | 18.2 | 23.1 | 40.3 | 55.5 |
| 3 | 9.0 | 13.5 | 17.6 | 20.3 | 25.3 | 40.9 | 57.1 |

EXAMPLE 5

Preparation of The Insoluble Carrier 10 g of the same chloroacetoamidomethylated fiber as in Example 1 was immersed in 300 ml of a 50% aqueous dimethylamine solution and heated to 40° C. for 10 hr.

The fiber was washed thoroughly with water to obtain dimethylaminoacetamidormethylated polystyrene fiber. The product had an ion exchange capacity of 2.68 milliequivalent/g. It showed a water content of 2.4 in a 0.07M phosphate buffer solution of pH 7.4. The water content was determined by swelling the fiber sufficiently, dehydrating the fiber by centrifugation, measuring its wet weight ($W_1$) and calculating the value according to the following equation:

Water content $= (W_1/W_0) - 1$ wherein $W_1$ has the same meaning as above and $W_0$ is dry weight of the fiber.

Preparation of the Blood-Treating Material 6 g of the above-mentioned tert-amino group-containing polystyrene fiber was immersed in 600 ml of a 0.07M phosphate buffer solution for an entire day and night to swell the fiber. The fiber was then mixed with 100 ml of 0.4 mg/ml aqueous solution of lipopolysaccharide obtained from Escherichia coli 055:B5 (produce of Difco Laboratories Co. obtained by extraction with trichloroacetic acid, protein content 10.0%). The obtained mixture was shaken at room temperature for 2 days. The fiber was taken out and washed with 200 ml of water three times. The fiber was then immersed in 200 ml of boiling water for 30 min. This immersion was repeated three times. The fiber was washed with a 0.07M phosphate buffer solution (pH 7.4) until the pH of the wash solution became 7.4 to obtain a fiber onto which the lipopolysaccharide was immobilized.

The concentrations of the lipopoly-saccharide in the immobilization mother liquor and the wash solution were determined by phenol/sulfuric acid method.

It was revealed that the amount of the lipopolysaccharide immobilized was 3.0 mg/g.

0.6 g of the above-mentioned lipopoly-saccharide-immobilized fiber was washed with 200 ml of isotonic sodium chloride solution and then immersed in 50 ml of the same solution. The resulting solution was heated to 38° C. for 3 hours. Thereafter, the amount of the lipopolysaccharide in the isotonic sodium chloride solution was determined by the Limulus-Pregel method. The amount was up to 1 ng/ml.

Biological Testing of The Blood-Treating Material

Fibrosarcoma MC-B1 was induced in BALB/C mice by innoculation with methylcholanthrene. $5 \times 10^5$ tumor cells were taken and subcutaneously injected into the backs of BALB/C mice (10 weeks old) to obtain tumor mice. The tumor grew to a size of 2.1 mm diameter in 5

TABLE II

| group of rabbits | average weight of rabbits (mm) | | | | | | | | | | |
|---|---|---|---|---|---|---|---|---|---|---|---|
| | — | 5 | 10 | 15 | 20 | 25 | 30 | 35 | 40 | 45 | 50 |
| 1* | 2.17 | 2.15 | 2.06 | 2.10 | 2.23 | 2.34 | 2.45 | 2.51 | 2.60 | 2.72 | 2.79 |
| 2 | 2.25 | 2.23 | 2.10 | 2.10 | 2.11 | 2.10 | 2.06 | 2.03 | 1.94 | 1.89 | 1.82 |
| 3 | 2.27 | 2.25 | 2.22 | 2.24 | 2.32 | 2.38 | 2.35 | 2.40 | 2.23 | 2.07 | 1.90 |

*according to the present invention days after the innoculation, 6.3 mm 10 days thereafter and 8.9 mm 12 days thereafter.

1.2 g of the lipopolysaccharide-immobilized fiber (containing 1.2 mg of the lipopolysaccharide) prepared above was added to 60 ml of BALB/C mouse serum. The mixture was shaken at 8 37° C. for 180 min and centrifuged to separate a supernatant liquid (activated serum).

21 tumor-bearing mice were divided into three groups 9 days after the innoculation, each group consisting of 7 mice. 0.5 ml of the activated serum diluted with 2.5 ml of isotonic sodium chloride solution was given to the mice of a first group by intraperitoneal injection once a day for 5 days (5 times). 0.5 ml of the activated serum diluted with 2.5 ml of the isotonic sodium chloride solution was given to the mice of a second group by intraperitoneal injection at intervals of 2 hrs. 5 times in total. The mice in a third group were not treated at all. 9 days and 45 days after the innoculation, the average tumor diameters were 4.7 mm and 23.3 mm in the first group, 4.7 mm and 20.5 mm in the second group and 4.8 mm and 29.0 mm in the third group. The number of the mice in which a reduction of the tumor was recognized was 2 in 7 mice in the first group, 4 in 7 mice in the second group and 0 in 7 mice in the third group. The number of completely cured mice was 0 in the first and third groups and 2 in the second group. The results in tabular form are as follows:

| Group | Avg. Time or Diameters(mm) | | Reduction in Tumor/# in Group | Mice Cured |
|---|---|---|---|---|
| | 9 days | 45 days | | |
| 1 | 4.7 | 23.3 | 2/7 | 0 |
| 2 | 4.7 | 20.5 | 4/7 | 2 |
| 3 | 4.8 | 29.0 | 0/7 | 0 |

EXAMPLE 6

Preparation of The Insoluble Carrier 10 g of the same chloroacetamidomethylated fiber as in Example 1 was immersed in 300 ml of a 90% aqueous ethanol solution containing 10 g of potassium iodide. After heating at 50° C. for 3 h, the fiber was washed with water and ethanol to obtain an iodoacetamidomethylated fiber. Then, the fiber was immersed in a liquid mixture of 50 ml of triethylamine and 50 ml of water and heated to 50° C. for 15 hrs. The fiber was washed with water, 1N-sodium hydroxide, water and a 1M aqueous common salt solution successively to obtain triethylammonium-acetamidomethylated polystyrene fiber. The fiber had a neutral salt decomposing capacity of 1.56 milliequivalents/g, total ion exchange capacity of 1.65 milliequivalents/g and a water content (pH 7.4) of 1.2 (calculated as in Example 5).

Preparation of The Blood-Treating Material 3 g of the above-mentioned tert-amino group-containing polystyrene fiber was immersed in 300 ml of isotonic sodium chloride solution for an entire day and night to swell the fiber. The fiber was then mixed with 50 ml of a 0.4 mg/ml aqueous solution of a lipopolysaccharide obtained from Escherichia coli 055:B5 (a product of Difco Laboratories Co. obtained by extraction with trichloroacetic acid). The obtained mixture was shaken at room temperature for 2 days. The fiber was taken out and washed with 100 ml of water three times. The fiber was then immersed in 100 ml of boiling water for 30 minutes. This immersion was repeated three times. The fiber was charged in a 15 mm chromatographic column and washed with 6 liters of water to obtain a lipopolysaccharide-immobilized fiber. The amount of the immobilized lipopolysaccharide was 4.0 mg/g of fiber.

0.6 g of the lipopolysaccharide-immobilized fiber was washed with 200 ml of isotonic sodium chloride solution according to the Japanese Pharmacopocia and then immersed in 50 ml of the isotonic sodium chloride solution. The resulting solution was heated to 38° C. for 3 hours. Thereafter, the amount of the lipopolysaccharide in said solution was determined by the Limulus-Pregel method. The amount was up to 1 ng/ml.

Biological Testing of The Blood Treating Material

Twenty milliliters of BALB/C mouse serum were mixed with 0.4 g of above-mentioned blood treating material.

The mixture was shaken at 37° C. for 60 min and centrifuged to separate an supernatant liquid (activated serum).

Thirty tumor-bearing mice (9 days after innoculation with the tumor cells) were obtained in the same manner as in Example 1. The mice were divided into three groups, each group consisting of 10 mice.

The activated serum diluted with 2.5 ml of isotonic sodium chloride solution was given to the mice of a first group by intraperitoneal injection 5 times at intervals of 2 hours. Three ml of the isotonic sodium chloride solution was given to the mice of a second group by intraperitoneal injection 5 times at intervals of 2 hours. The mice in the third group were not treated. Nine days and 45 days after the innoculation, the average tumor diameters were 4.9 mm and 18.8 mm in the first group, 4.7 mm and 22.0 mm in the second group and 4.9 mm and 23.6 mm in the third group. The number of the mice in which a reduction of the tumor was recognized were 5 in 10 in the first group, and 1 in 10 mice in the second and third groups. The number of completely cured mice was 0 in the second and the third groups and 2 in the first group. The results are summarized as follows:

| Group | Avg. Tumor Diameters (mm) | | Reduction in Tumor Size per Number of Mice | Mice Cured |
|---|---|---|---|---|
| | 9 days | 45 days | | |
| 1 | 4.9 | 18.8 | 5/10 | 2 |
| 2 | 4.7 | 22.0 | 1/10 | 0 |
| 3 | 4.9 | 23.6 | 1/10 | 0 |

In another aspect of the invention, as illustrated in the following examples and appended Figures, the animal is "primed" or pre-treated with one or more biological response modifiers prior to extracorporeal perfusion and contact with the blood-treating material. Suitable biological response modifiers (BRM's) include, by general class, the imunoactivators, such as Bacillus Calmette-Guerin cells (BCG), OK-432 cells and muramyl dipeptide (MDP); the interferons, alpha, beta, gamma, etc., either isolated or the product of recombinant procedures, and inducers of interferon; the lymphokines, such as IL-1, IL-2, IL-3, etc., including interleukins prepared by recombinant techniques; and various cytokines as illustrated by tumor necrosis factor (TNF). Among these biological response modifiers the imunoactivators as a class are preferred, with BCG and OK-432 most preferred.

EXAMPLE 7

BCG-inoculated rabbits were prepared by injecting male Japanese White rabbits weighing 2.2 to 2.6 kg (CLER JAPAN INC. Osaka) intravenously with $1 \times 10^{*}8$ viable Bacillus Calmette-Guerin cell (Nippon BCG Kyokai, Tokyo).

Tumor-bearing rabbits were obtained by intramuscular injection of $1 \times 10^{*}6$ viable $V \times 2$ tumor cells (as assessed by trypan blue dye exclusion) in 0.3 ml of phosphate buffered saline containing 10% fetal calf serum, 1 cm deep into the thigh muscle of the left hind limb of 17 BCG-inoculated rabbits the next day after BCG-inoculation or 2 non-BCG-inoculated rabbits.

Blood treating columns were prepared by filling 0.8 g of bundled blood-treating material (prepared in Example 1) into the column (1.0 cm-diameter, 3.8 cm-length: 3 ml-volume).

As shown in Table 1, twelve tumor-bearing rabbits (BCG-inoculated) were anesthetized with Somnopentyl (Pitman-Moore. U.S.A.; 40 mg/kg-body weight, intrapenitorial injection) and underwent extracorporeal perfusion through the above-mentioned blood-treating columns at a flow rate of 15 ml/min. for 90 minutes by canulation of the femoral artery and the aural vein. Heparin (500 units/kg-body weight of rabbit) was added into the circuit at the beginning of the perfusion. After the sutur, the survival rate of the rabbits and the size of the tumor (the thickness of the thigh muscle) were observed.

TABLE 1

```
        Protocol of experiment
days  0   1                    14
Viable BCG  VX2              DHP      Treated(12)
                                      Control(5)
                                      nontreated(2)
DHP: direct hemoperfusion
```

For Control group, five tumor-bearing rabbits were observed without extracorporeal perfusion. And 2 tumor-bearing rabbits (non-BCG-inoculated) rabbits were also observed without perfusion for Non-treated group.

Change of tumor-size (thickness of the thigh muscle) and survival rate of the rabbits were shown in Table 2 and Table 3 respectively.

TABLE 2

| | Change of tumor-size | | | |
| --- | --- | --- | --- | --- |
| | Thickness of the thigh muscle Days after tumor-implantation | | | |
| | −1 | 13 | 29 | 46 |
| Treated group (BCG + DHP) | 20.0 + 0.6 (n = 12) | 23.0 + 0.6 (n = 12) | 20.1 + 1.3 (n = 10) | 16.0 + 0.4 (n = 8) |
| Control group (BCG) | 19.6 + 0.5 (n = 5) | 22.5 + 1.0 (n = 5) | 28.3 + 4.3 (n = 4) | 15.5 + 2.5 (n = 2) |
| Non-treated group | 20.0 + 1.0 (n = 2) | 30.0 + 3.0 (n = 2) | 41.0 + 3.0 (n = 2) | 56.0 (n = 1) |

TABLE 3

| Survival rate of the rabbits at 46 days at tumor-implantation | | |
| --- | --- | --- |
| Treated group | 8/12 | (67%) |
| Control group | 2/5 | (40%) |

TABLE 3-continued

| Survival rate of the rabbits at 46 days at tumor-implantation | | |
| --- | --- | --- |
| Non-treated group | 0/2 | (0%) |

Two of 2 Non-treated rabbits and 3 of 5 Control rabbits were died at 46 days after tumor-implantation. On the otherhand, 8 of 12 treated rabbits were alive at that time. Tomor growth were significantly suppressed in treated rabbits.

These results indicate that the blood-treating material of the present invention is effective for the treatment of the tumor-bearing rabbit.

EXAMPLE 8

OK-priming rabbits were prepared by injecting male Japanese White rabbits weighing 2.2 to 2.6 kg intravenously with 30 KE of OK-432 (Chugai Seiyaku K.K.).

Tumor-bearing rabbits were obtained by intramuscular injection of $1 \times 10^{*}6$ viable $V \times 2$ tumor cells (as assessed by trypan blue dye exclusion) in 0.3 ml of phosphate buffered saline containing 10% fetal calf serum, 1 cm deep into the thigh muscle of the left hind limb of OK-priming rabbits the next day after OK-432-injection.

Blood treating columns were prepared by filling 0.8 g of bundled blood-treating material or carrier (Example 1) into the same colomn as in Example 8.

Tumor-bearing rabbits (OK432-primed) were anesthetized with Somnopentyl (intraperitorial injection) and underwent extracorporeal perfusion through the above-mentioned blood-treating columns at a flow rate of 15 ml/min. for 1 hr by canulation of the femoral artery and the aural vein. Heparin (500 units/kg-body weight of rabbit) was added into the circuit at the beginning of the perfusion. After the sutur, the survival rate of the rabbits was observed.

As shown in Table 4, OK-priming rabbits were treated with blood treating columns (filled with blood-treating material) at 11 days after tumor-implantation for Treated group, and twice at 8 days and 15 days for Double treated group. For Sham treated group 5 tumor-bearing rabbits were treated with the columns (filled with carrier) at 14 days. Four tumor-bearing rabbits were observed without extracorporial perfusion.

TABLE 4

```
            Protocol of experiment
days  −1  0    8    11   14   15
      OK-432 VX2  DHP  DHP       DHP    Treated(8)
                              DHP        Double treated(7)
                                         Sham treated(5)
                                         Non-treated(4)
DHP: direct hemoperfusion
```

Figure 2:
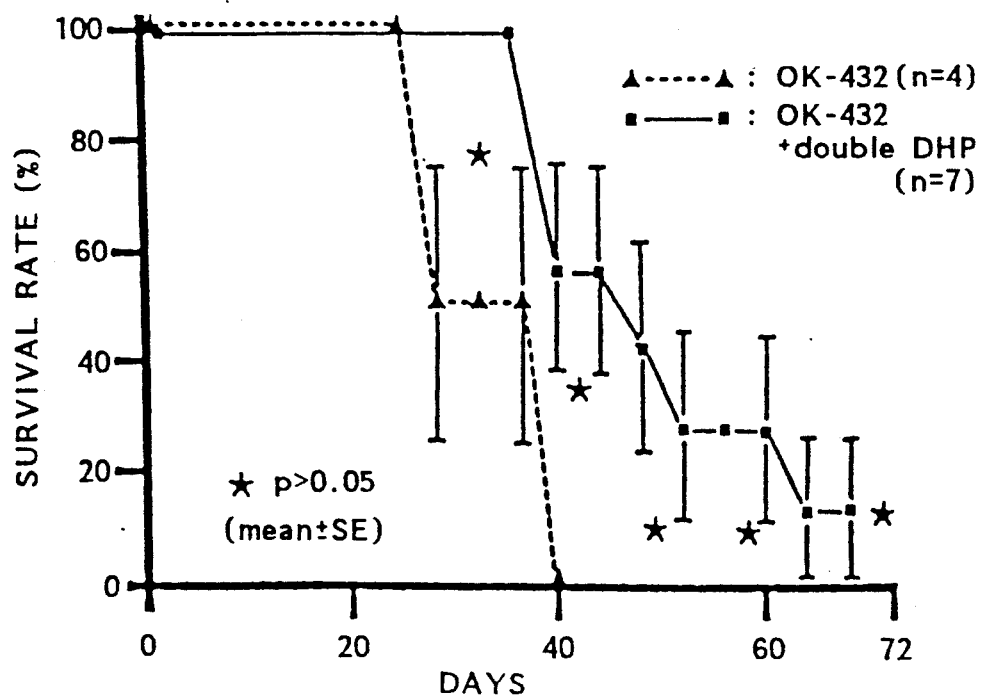
FIG. 2 is a graph showing the survival rate of V×2 tumor-bearing rabbits.

Survival rates were shown in FIG. 1 for Treated group and Sham treated group, and in FIG. 2 for Double treated group and Non-treated group respectively.

All non-treated rabbits and Sham treated rabbits were died at 40 days after tumor-implantation. On the otherhand, 4 of 8 Treated rabbits and 4 of 7 Double treated rabbits were alive at that time.

These results indicate that the blood-treating material of the present invention is effective for the treatment of the tumor-bearing rabbit.

What is claimed is:

1. A method of treating an animal having a malignant tumor comprising contacting whole blood, blood plasma or blood serum with a blood-treating material composed of a lipopolysaccharide derived from cell walls of Gram-negative bacteria said lipopolysaccharide immobilized on an insoluble carrier, wherein the insoluble carrier is selected from the group consisting of styrene, styrene divinylbenzene copolymer, a methylene-crosslinked styrene divinylbenzene copolymer, a sulfone-crosslinked styrene divinylbenzene copolymer, an acrylic acid acrylonitrile copolymer, an acrylic acid styrene copolymer, nylon-6, nylon-6,6, polyethylene terephthalate, a carboxyl group containing insolubilized cellulose, and aminoethylated cellulose.

2. A method of treating an animal having a malignant tumor according to claim 1, comprising contacting whole blood, blood plasma or blood serum with a blood-treating material composed of a lipopolysaccharide derived from cell walls of Gram-negative bacteria and having a protein content of from about 0.1 to about 50%, the lipopolysaccharide immobilized on an insoluble carrier.

3. A method of treating an animal having a malignant tumor according to claim 1, comprising contacting whole blood, blood plasma or blood serum with a blood-treating material composed of a lipopolysaccharide derived from cell walls of Gram-negative bacteria and having a protein content of from about 0.1 to about 20%, the lipopolysaccharide immobilized on an insoluble carrier.

* * * * *